US00PP08735P

United States Patent [19]

Gutbier

[11] Patent Number: Plant 8,735

[45] Date of Patent: May 17, 1994

[54] POINSETTIA PLANT GUTBIER MARLENE

[75] Inventor: Gregor Gutbier, Linz/Rhein, Fed. Rep. of Germany

[73] Assignee: Paul Ecke Ranch, Inc., Encinitas, Calif.

[21] Appl. No.: 56,210

[22] Filed: Apr. 30, 1993

[51] Int. Cl.[5] ..... A01H 5/00

[52] U.S. Cl. ..... Plt./86.4

[58] Field of Search ..... Plt. 86.4

*Primary Examiner*—James R. Feyrer

*Attorney, Agent, or Firm*—Arnold, White & Durkee

[57] ABSTRACT

Gutbier Marlene is a new cultivar distinguished by bright brick red bracts, self branching and compact growth habit. The new plant is tolerant to temperatures down to 10° C. showing intensified bract color under cool conditions. Bract retention is long, typically lasting for several months.

1 Drawing Sheet

BACKGROUND OF THE NEW PLANT

Gutbier Marlene is a strong growing Poinsettia of short to medium height. It has self-branching traits which make it desirable for branched plant production. Because of its compact growth habit, it can be flowered without the use of chemical growth retardants. Gutbier Marlene is in "full-bloom" 9 weeks after flower induction. The bright brick-red bracts have a horizontal presentation, with the smaller inner bracts at a slightly upward angle. The bract petioles are relatively short, forming a tight circle of bracts around the cyathia. Bract retention lasts for several months. After flowering, Gutbier Marlene can withstand temperatures down to 10 degrees C. very well, and these conditions intensify its bract color.

This new Poinsettia cultivar originated as a seedling from cross pollination of cultivar 236 and '268' (U.S. Plant Pat. No. 7,275) in my greenhouse in Linz, Germany. It was selected because of its large, erect, bright brick-red flower bracts. It has self-branching traits and a compact growth habit which seems to make it a desirable plant for commercial greenhouse production. No chemical growth retardant may be needed to produce a flowering plant of desired height. After selection, the plant was vegetatively reproduced by stem cuttings at the same location. Successive generations of vegetative propagation demonstrated its distinct characteristics are firmly fixed and held true from generation to generation.

Gutbier Marlene is distinctly different from its parent '268' (U.S. Plant Pat. No. 7,275) in leaf color, bract color and bract orientation. The leaf color of Gutbier Marlene is darker than RHS 147A; '268' is near RHS 147A. The bract color of Gutbier Marlene is bright brick red, near RHS 45B; '268' bracts are bright red, darker than RHS 46B or RHS 45A. The bract orientation on Gutbier Marlene is mostly horizontal while '268' bracts are oriented upward from horizontal. In 1992, vegetative cuttings were sent to Encinitas, Calif. for further testing under greenhouse conditions there.

DESCRIPTION OF THE PHOTOGRAPHS

Poinsettia cultivar Gutbier Marlene is illustrated in the accompanying color photographs.

The upper photo is a side view of a typical pot containing three unpinched flowering plants.

The lower photo is a top view of the same plants showing flower and bract formation.

DESCRIPTION OF THE PLANT

The poinsettia cultivar Gutbier Marlene was grown in greenhouses in Encinitas, Calif. from September to December 1992. Under natural daylength conditions, the flowers reached maturity on Dec. 5, 1992. At that time the following information was observed and recorded.

The plants were grown in 17 cm pots, three plants per pot, as single stem plants (not pinched) so that one large flower terminated each stem. There were 6–7 side branches on each stem which terminated in small flowers. The overall height of the plants, including the pot, was 35 cm. The width of each bract presentation was 34 cm in diameter. Color designations are from the 1986 edition of the R.H.S. Colour Chart, first published in 1966 by The Royal Horticultural Society, London, England.

Gutbier Marlene has not been observed under all possible environmental conditions. The phenotype may vary with variations in the environment such as light intensity, temperature and daylength.

The following characteristics have been repeatedly observed and are determined to be basic characteristics of Gutbier Marlene, which in combination distinguish this poinsettia as a new and distinct cultivar.

THE PLANT

Origin: Seedling from cross pollination.

*Female parent.*—Seedling 236.

*Pollen parent.*—Cultivar 268 (U.S. Plant Pat. No. 7,275).

Classification:

*Botanic.*—*Euphorbia pulcherrima* Willd.

*Common name.*—Poinsettia.

*Cultivar name.*—"Gutbier Marlene".

Form: Shrub.

Height: Short to medium.

Growth habit: As a single stemmed plant, upright and vigorous. In full flower, the stem is terminated by a large inflorescence, with 6–7 smaller flowering side shoots lower on the stem. The average overall height of single stemmed plants was 35 cm at flowering.

Branching: "Gutbier Marlene" is a self-branching poinsettia, but branching vigor can be enhanced by removal of the stem tip before flower initiation. Then several flowering branches with equal vigor will develop on a single plant.

Growth rate: Very fast. Rooting of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being 13–14 cm long and about 8–9 cm wide with leaf petiles 5–6 cm long.

*Leaf shape.*—Typical leaves are ovate with acute to obtuse bases and acuminate tips. Leaf margins are entire to modestly lobed with usually one lobe on either side of the leaf blade.

*Leaf surface.*—Upper surface is glabrous and slightly rugose. The under surface is slightly pubescent.

*Leaf color.*—Upper side — Darker than RHS 147A. Under side — Near 147B.

*Retention.*—The foliage retention is good even under low light intensities in the consumer's home.

Bracts: Generally there are three primary bracts and about 15 secondary bracts of various sizes subtending the cyathia. The primary bracts have blades typically 15–17 cm. long and about 10–11 cm. wide.

*Shape.*—The primary bracts are mostly ovate with acute bases and acuminate tips. There is usually one lobe on either side of the bracts. The secondary bracts are mostly elliptic with entire margins.

*Surface.*—The bract surface is slightly rugose.

*Color.*—Upper side — Bright orange-red. Near RHS 45B. Underside — Light red. Near RHS 47B, but overlaid with a greenish-white color near RHS 1D. This gives the bracts a greenish white appearance on the under side.

Cyathia: Generally, about 16 cyathia (flowers) develop when the plant is in "full bloom." Each cyathium is 7–8 mm long and 6 mm wide, green in color and fringed with red at the distal end. The green pedicles are about 5 mm long. The stamens are red and the anthers are bifurcate. The pollen is yellow and copious. The stigmas are dark red and trifurcate. There is one yellow nectar cup protruding from the side of each cyathium.

Disease resistance: Relatively unaffected by Botrytis.

Post production: "Gutbier Marlene" withstands transportation conditions very well in comparison to other Poinsettia cultivars. As a blooming plant, it can take lower temperatures down to 10 degrees C., and these conditions intensify its bract color.

What is claimed is:

1. A new and distinct poinsettia cultivar, substantially as herein described and shown, characterized by its brick-red bract color, vigorous self branching and compact habit.

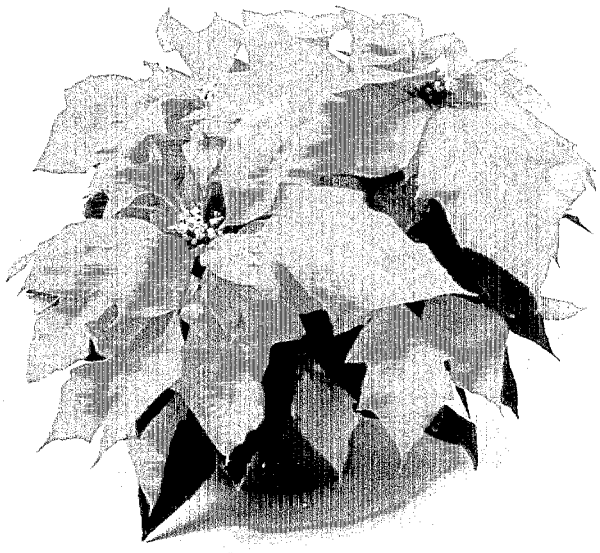
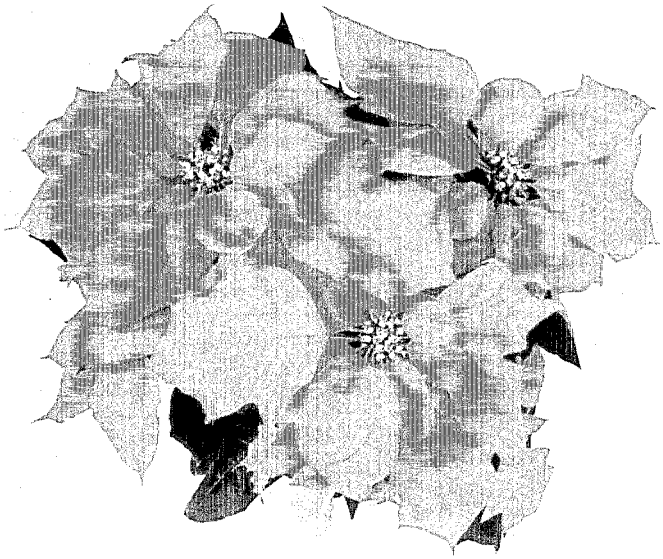

* * * * *